(12) United States Patent
Lu et al.

(10) Patent No.: US 11,186,543 B2
(45) Date of Patent: Nov. 30, 2021

(54) CRYSTALLINE FORM OF 3-((L-VALYL)AMINO))-3,3-DIDEUTERIUM-1-PROPANESULFONIC ACID, PREPARATION METHOD AND USES THEREOF

(71) Applicant: RISEN (SUZHOU) PHARMA TECH CO., LTD., Jiangsu (CN)

(72) Inventors: Jiasheng Lu, Suzhou (CN); Jiamin Gu, Suzhou (CN); Daiqiang Hu, Suzhou (CN); Xianqi Kong, Suzhou (CN)

(73) Assignee: RISEN (SUZHOU) PHARMA TECH CO., LTD., Suzhou (CN)

( * ) Notice: Subject to any disclaimer, the term of this patent is extended or adjusted under 35 U.S.C. 154(b) by 0 days.

(21) Appl. No.: 16/960,056

(22) PCT Filed: Dec. 28, 2018

(86) PCT No.: PCT/CN2018/124729
§ 371 (c)(1),
(2) Date: Jul. 3, 2020

(87) PCT Pub. No.: WO2019/134584
PCT Pub. Date: Jul. 11, 2019

(65) Prior Publication Data
US 2021/0053914 A1 Feb. 25, 2021

(30) Foreign Application Priority Data
Jan. 4, 2018 (CN) .......... 201810007023.3

(51) Int. Cl.
*C07C 309/15* (2006.01)

(52) U.S. Cl.
CPC ........ *C07C 309/15* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 8,748,656 B2 | 6/2014 | Kong et al. |
| 9,499,480 B2 | 11/2016 | Kong et al. |
| 10,238,611 B2 | 3/2019 | Kong et al. |
| 10,471,029 B2 | 11/2019 | Tolar et al. |
| 10,472,323 B2 | 11/2019 | Lu et al. |
| 10,857,109 B2 | 12/2020 | Kong et al. |
| 10,954,188 B2 | 3/2021 | Lu et al. |

(Continued)

FOREIGN PATENT DOCUMENTS

| | | |
|---|---|---|
| CN | 101600730 A | 12/2009 |
| CN | 108623501 A | 3/2017 |

(Continued)

OTHER PUBLICATIONS

International Search Report and Written Opinion issued in corresponding International application No. PCT/CN2018/124729 dated Mar. 25, 2019.

(Continued)

*Primary Examiner* — Sudhakar Katakam
*Assistant Examiner* — Jennifer C Sawyer
(74) *Attorney, Agent, or Firm* — BCF LLP

(57) ABSTRACT

The present invention relates to a crystalline form of compound 3-((L-valyl)amino)-3,3-dideuterium-1-propanesulfonic acid, preparation method and uses thereof.

24 Claims, 5 Drawing Sheets

(56) References Cited

U.S. PATENT DOCUMENTS

| | | |
|---|---|---|
| 2009/0076167 A1 | 3/2009 | Czarnik |
| 2010/0120744 A1 | 5/2010 | Gant |

FOREIGN PATENT DOCUMENTS

| | | |
|---|---|---|
| WO | 2009019534 A2 | 2/2000 |
| WO | 2017044840 A1 | 3/2017 |
| WO | 2018170590 A1 | 9/2018 |

OTHER PUBLICATIONS

Foster, A.B., Deuterium Isotope Effects in the Metabolism of Drugs and Xenobiotics: Implications for Drug Design, Advances in Drug Research, vol. 14, pp. 1-40, 1985.

Office Action issued in corresponding Chinese application No. 201810007023.3 dated Mar. 12, 2021.

CRYSTALLINE FORM OF 3-((L-VALYL)AMINO))-3,3-DIDEUTERIUM-1-PROPANESULFONIC ACID, PREPARATION METHOD AND USES THEREOF

CROSS-REFERENCE TO RELATED APPLICATIONS

This application is a U.S. National Stage Application under 35 U.S.C. § 371 of International Application No. PCT/CN2018/124729, filed Dec. 28, 2018, which claims priority to Chinese Application No. 201810007023.3, filed Jan. 4, 2018, the entire contents of each of which are hereby incorporated by reference in their entireties.

TECHNICAL FIELD

The present invention relates to a crystalline form of compound 3-((1-valyl)amino)-3,3-dideuterium-1-propanesulfonic acid, preparation method and use thereof.

BACKGROUND

The preparation of the compound 3-((L-valyl)amino)-3,3-dideuterium-1-propanesulfonic acid and its pharmaceutical use are disclosed in Chinese patent application No. 201710168819.2 by the present applicant, the entirety of which is incorporated herein by reference. Said compound 3-((L-valyl)amino)-3,3-dideuterium-1-propanesulfonic acid can also be prepared according to the method described in Example 1 below.

SUMMARY OF THE INVENTION

An object of the present invention is to provide a novel crystalline form of compound 3-((L-valyl)amino)-3,3-dideuterium-1-propanesulfonic acid (hereinafter also referred to as Crystalline Form A), which crystalline form has beneficial properties compared to the compounds disclosed in Chinese patent application No. 201710168819.2. Said beneficial properties may include higher thermodynamic stability, lower hygroscopicity, better flow properties, better reproducibility in manufacturing, higher purity, compliance with quality requirements of pharmaceutical preparations, long-term preservation, and application to production of formulations.

The present invention provides a crystalline form of compound 3-((L-valyl)amino)-3,3-dideuterium-1-propanesulfonic acid. The crystalline form exhibits characteristic diffraction peaks at 2θ diffraction angles of 9.1°, 11.0°, 15.6°, 18.2°, 20.7°, and 22.2° in an X-ray powder diffraction pattern using Cu—Kα as a radiation source, wherein 2θ has an error range of ±0.2°.

In an embodiment, preferably, said crystalline form exhibits characteristic diffraction peaks at 2θ diffraction angles of 9.1°, 11.0°, 14.6°, 15.6°, 16.3°, 17.5°, 18.2°, 19.1°, 20.7°, 22.2°, 22.7°, and 25.4° in the X-ray powder diffraction pattern, wherein 2θ has an error range of ±0.2°.

In an embodiment, preferably, said crystalline form exhibits characteristic diffraction peaks at 2θ diffraction angles of 9.1°, 11.0°, 14.6°, 15.6°, 16.3°, 17.5°, 18.2°, 19.1°, 20.7°, 21.3°, 22.2°, 22.7°, 24.9°, 25.4°, 28.9°, 30.1°, 32.1°, and 34.2° in the X-ray powder diffraction pattern, wherein 2θ has an error range of ±0.2°.

In an embodiment, preferably, said crystalline form (substantially) has an X-ray powder diffraction pattern as shown in FIG. 2.

In an embodiment, said crystalline form has a space group of $P4_32_12$, unit cell dimensions: a=11.1989(4) Å, α=90°, b=11.1989(4) Å, β=90°, c=18.2479(7) Å, γ=90°, Z=8, and has a unit cell volume of 2288.57(19) Å3.

In an embodiment, said crystalline form belongs to a tetragonal system.

In an embodiment, said crystalline form has a crystal size of 0.200×0.200×0.150 mm$^3$.

In an embodiment, preferably, said crystalline form has a melting point of 319° C. as measured by differential scanning calorimetry.

Another object of the present invention is to provide a method for preparing the crystalline form of compound 3-((L-valyl)amino)-3,3-dideuterium-1-propanesulfonic acid as described above, said method comprising the following steps: dissolving the compound 3-((L-valyl)amino)-3,3-dideuterium-1-propanesulfonic acid in a first solvent selected from a group consisting of water and dimethyl sulfoxide to obtain a clear solution; and adding a second solvent, stirring, precipitating crystals to obtain said crystalline form, wherein the first solvent is different from the second solvent.

In an embodiment, preferably, said method comprises the following steps: dissolving the compound 3-((L-valyl)amino)-3,3-dideuterium-1-propanesulfonic acid in a first solvent selected from the group consisting of water and dimethyl sulfoxide, optionally heating to 30-80° C., adding a second solvent with stirring, optionally cooling to 60° C. to −20° C. and stirring (e.g., for 0.5-24 hours), followed by crystallization to obtain said crystalline form.

In an embodiment, preferably, said second solvent is one or more selected from the group consisting of alcohols, nitriles, esters, ketones, ethers, alkanes, halogenated alkanes, aromatic hydrocarbons, organic acids, sulfoxides, amides, and nitromethane solvent.

In an embodiment, preferably, said second solvent is one or more selected from a group consisting of methanol, ethanol, n-propanol, isopropanol, n-butanol, sec-butanol, ethylene glycol, glycerol, benzyl alcohol, trifluoroethanol, acetonitrile, propionitrile, butyronitrile, isobutyronitrile, ethyl formate, propyl formate, isopropyl formate, methyl acetate, ethyl acetate, isopropyl acetate, acetone, butanone, 2-pentanone, ethyl ether, isopropyl ether, methyl tert-butyl ether, tetrahydrofuran, 1,4-dioxane, n-hexane, n-heptane, methylcyclohexane, dichloromethane, chloroform, toluene, acetic acid, dimethyl sulfoxide, N,N-dimethylformamide, N,N-dimethylacetamide, and nitromethane.

In an embodiment, preferably, a volume ratio of said first solvent to said second solvent is 1:1-1:200 (particularly, the volume ratio may be, for example, 1:1, 1:2-1:200, 1:3-1:200, 1:4-1:200, 1:5-1:200, 1:6-1:200, 1:7-1:200, 1:8-1:200, 1:9-1:200, 1:10-1:200, 1:11-1:200, 1:12-1:200, 1:13-1:200, 1:14-1:200, 1:15-1:200, 1:16-1:200, 1:17-1:200, 1:18-1:200, 1:19-1:200, 1:20-1:200, 1:21-1:200, 1:22-1:200, 1:23-1:200, 1:24-1:200, 1:25-1:200, 1:26-1:200, 1:27-1:200, 1:28-1:200, 1:29-1:200, 1:30-1:200, 1:35-1:200, 1:40-1:200, 1:45-1:200, 1:50-1:200, 1:55-1:200, 1:60-1:200, 1:65-1:200, 1:70-1:200, 1:75-1:200, 1:80-1:200, 1:85-1:200, 1:90-1:200, 1:95-1:200, 1:100-1:200, 1:110-1:200, 1:120-1:200, 1:130-1:200, 1:140-1:200, 1:150-1:200, 1:160-1:200, 1:170-1:200, 1:180-1:200, 1:190-1:200, or 1:200); and/or, a mass-to-volume ratio of said compound 3-((L-valyl)amino)-3,3-dideuterium-1-propanesulfonic acid to the total solvent is 10 mg:0.05 ml-100 mg:250 ml (particularly, the mass-to-volume ratio may be, for example, 100 mg:0.5 ml, 100 mg:0.6 ml-100 mg:250 ml, 100 mg:0.7 ml-100 mg:250 ml, 100 mg:0.8 ml-100 mg:250 ml, 100 mg:0.9 ml-100 mg:250 ml, 100 mg:1.0 ml-100 mg:250 ml, 100 mg:1.5 ml-100 mg:250 ml, 100 mg:2.0 ml-100 mg:250 ml, 100 mg:2.5 ml-100 mg:250 ml, 100 mg:3.0 ml-100 mg:250 ml, 100 mg:3.5 ml-100 mg:250 ml, 100 mg:4.0 ml-100 mg:250 ml, 100 mg:4.5 ml-100 mg:250 ml, 100 mg:5.0 ml-100 mg:250 ml, 100 mg:5.5 ml-100 mg:250 ml, 100 mg:6.0 ml-100 mg:250 ml, 100 mg:6.5 ml-100 mg:250 ml, 100 mg:7.0 ml-100 mg:250 ml, 100 mg:7.5 ml-100 mg:250 ml, 100 mg:8.0 ml-100 mg:250 ml, 100 mg:8.5 ml-100 mg:250 ml, 100 mg:9.0 ml-100 mg:250 ml, 100 mg:9.5 ml-100 mg:250 ml, 100 mg:10.0 ml-100 mg:250 ml, 100 mg:10.5 ml-100 mg:250 ml, 100 mg:11.0 ml-100 mg:250 ml, 100 mg:11.5 ml-100 mg:250 ml, 100 mg:12.0 ml-100 mg:250 ml, 100 mg:12.5 ml-100 mg:250 ml, 100 mg:13.0 ml-100 mg:250 ml, 100 mg:13.5 ml-100 mg:250 ml, 100 mg:14.0 ml-100 mg:250 ml, 100 mg:14.5 ml-100 mg:250 ml, 100 mg:15.0 ml-100 mg:250 ml, 100 mg:15.5 ml-100 mg:250 ml, 100 mg:16.0 ml-100 mg:250 ml, 100 mg:16.5 ml-100 mg:250 ml, 100 mg:17.0 ml-100 mg:250 ml, 100 mg:17.5 ml-100 mg:250 ml, 100 mg:18.0 ml-100 mg:250 ml, 100 mg:18.5 ml-100 mg:250 ml, 100 mg:19.0 ml-100 mg:250 ml, 100 mg:19.5 ml-100 mg:250 ml, 100 mg:20 ml-100 mg:250 ml, 100 mg:30 ml-100 mg:250 ml, 100 mg:35 ml-100 mg:250 ml, 100 mg:40 ml-100 mg:250 ml, 100 mg:45 ml-100 mg:250 ml, 100 mg:50 ml-100 mg:250 ml, 100 mg:55 ml-100 mg:250 ml, 100 mg:60 ml-100 mg:250 ml, 100 mg:65 ml-100 mg:250 ml, 100 mg:70 ml-100 mg:250 ml, 100 mg:75 ml-100 mg:250 ml, 100 mg:80 ml-100 mg:250 ml, 100 mg:85 ml-100 mg:250 ml, 100 mg:90 ml-100 mg:250 ml, 100 mg:95 ml-100 mg:250 ml, 100 mg:100 ml-100 mg:250 ml, 100 mg:105 ml-100 mg:250 ml, 100 mg:110 ml-100 mg:250 ml, 100 mg:120 ml-100 mg:250 ml, 100 mg:130 ml-100 mg:250 ml, 100 mg:140 ml-100 mg:250 ml, 100 mg:150 ml-100 mg:250 ml, 100 mg:160 ml-100 mg:250 ml, 100 mg:170 ml-100 mg:250 ml, 100 mg:180 ml-100 mg:250 ml, 100 mg:190 ml-100 mg:250 ml, 100 mg:200 ml-100 mg:250 ml, 100 mg:210 ml-100 mg:250 ml, 100 mg:220 ml-100 mg:250 ml, 100 mg:230 ml-100 mg:250 ml, 100 mg:240 ml-100 mg:250 ml, or 100 mg:250 ml), wherein said total solvent is the sum of said first solvent and second solvent.

In an embodiment, preferably, before adding the second solvent, a solution of the 3-((L-valyl)amino)-3,3-dideuterium-1-propanesulfonic acid in the first solvent is heated to a temperature of 30-80° C. (particularly, the temperature may be, for example, 35-80° C., 40-80° C., 45-80° C., 50-80° C., 55-80° C., 60-80° C., 65-80° C., or 70-80° C.).

In an embodiment, preferably, after adding the second solvent, the solution is cooled to a temperature of 60° C. to −20° C. (particularly, the temperature may be, for example, 55° C. to −20° C., 50° C. to −20° C., 45° C. to −20° C., 40° C. to −20° C., 35° C. to −20° C., 30° C. to −20° C., 25° C. to −20° C., 20° C. to −20° C., 15° C. to −20° C., 10° C. to −20° C., 5° C. to −20° C., 0° C. to −20° C., −5° C. to −20° C., −10° C. to −20° C., or −15° C. to −20° C.).

In an embodiment, preferably, precipitation of said crystalline form is followed by filtering and drying.

In an embodiment, in the method for preparing the crystalline form of compound 3-((L-valyl)amino)-3,3-dideuterium-1-propanesulfonic acid, said method comprises the following steps: dissolving the compound 3-((L-valyl)amino)-3,3-dideuterium-1-propanesulfonic acid in a first solvent to obtain a clear solution, adding a second solvent, and allowing the solution to stand until it volatilizes to precipitate crystals, thereby obtaining the crystalline form. In an embodiment, said first solvent is water, and said second solvent is one or more selected from the group consisting of alcohols, nitriles, esters, ketones, and ethers solvents.

In an embodiment, preferably, said second solvent is one or more selected from a group consisting of methanol, ethanol, n-propanol, isopropanol, n-butanol, sec-butanol, trifluoroethanol, acetonitrile, propionitrile, butyronitrile, isobutyronitrile, ethyl formate, propyl formate, isopropyl formate, methyl acetate, ethyl acetate, isopropyl acetate, acetone, butanone, 2-pentanone, ethyl ether, isopropyl ether, methyl tert-butyl ether, tetrahydrofuran, and 1,4-dioxane.

In an embodiment, preferably, a volume ratio of said first solvent to said second solvent is 1:1-1:100 (particularly, the volume ratio may be, for example, 1:1, 1:2-1:100, 1:3-1:100, 1:4-1:100, 1:5-1:100, 1:6-1:100, 1:7-1:100, 1:8-1:100, 1:9-1:100, 1:10-1:100, 1:11-1:100, 1:12-1:100, 1:13-1:100, 1:14-1:100, 1:15-1:100, 1:16-1:100, 1:17-1:100, 1:18-1:100, 1:19-1:100, 1:20-1:100, 1:21-1:100, 1:22-1:100, 1:23-1:100, 1:24-1:100, 1:25-1:100, 1:26-1:100, 1:27-1:100, 1:28-1:100, 1:29-1:100, 1:30-1:100, 1:35-1:100, 1:40-1:100, 1:45-1:100, 1:50-1:100, 1:55-1:100, 1:60-1:100, 1:65-1:100, 1:70-1:100, 1:75-1:100, 1:80-1:100, 1:85-1:100, 1:90-1:100, 1:95-1:100, or 1:100); and/or, a mass-to-volume ratio of said compound 3-((L-valyl)amino)-3,3-dideuterium-1-propanesulfonic acid to the total solvent is 10 mg:0.05 ml-100 mg:250 ml (particularly, the mass-to-volume ratio may be, for example, 100 mg:0.5 ml, 100 mg:0.6 ml-100 mg:250 ml, 100 mg:0.7 ml-100 mg:250 ml, 100 mg:0.8 ml-100 mg:250 ml, 100 mg:0.9 ml-100 mg:250 ml, 100 mg:1.0 ml-100 mg:250 ml, 100 mg:1.5 ml-100 mg:250 ml, 100 mg:2.0 ml-100 mg:250 ml, 100 mg:2.5 ml-100 mg:250 ml, 100 mg:3.0 ml-100 mg:250 ml, 100 mg:3.5 ml-100 mg:250 ml, 100 mg:4.0 ml-100 mg:250 ml, 100 mg:4.5 ml-100 mg:250 ml, 100 mg:5.0 ml-100 mg:250 ml, 100 mg:5.5 ml-100 mg:250 ml, 100 mg:6.0 ml-100 mg:250 ml, 100 mg:6.5 ml-100 mg:250 ml, 100 mg:7.0 ml-100 mg:250 ml, 100 mg:7.5 ml-100 mg:250 ml, 100 mg:8.0 ml-100 mg:250 ml, 100 mg:8.5 ml-100 mg:250 ml, 100 mg:9.0 ml-100 mg:250 ml, 100 mg:9.5 ml-100 mg:250 ml, 100 mg:10.0 ml-100 mg:250 ml, 100 mg:10.5 ml-100 mg:250 ml, 100 mg:11.0 ml-100 mg:250 ml, 100 mg:11.5 ml-100 mg:250 ml, 100 mg:12.0 ml-100 mg:250 ml, 100 mg:12.5 ml-100 mg:250 ml, 100 mg:13.0 ml-100 mg:250 ml, 100 mg:13.5 ml-100 mg:250 ml, 100 mg:14.0 ml-100 mg:250 ml, 100 mg:14.5 ml-100 mg:250 ml, 100 mg:15.0 ml-100 mg:250 ml, 100 mg:15.5 ml-100 mg:250 ml, 100 mg:16.0 ml-100 mg:250 ml, 100 mg:16.5 ml-100 mg:250 ml, 100 mg:17.0 ml-100 mg:250 ml, 100 mg:17.5 ml-100 mg:250 ml, 100 mg:18.0 ml-100 mg:250 ml, 100 mg:18.5 ml-100 mg:250 ml, 100 mg:19.0 ml-100 mg:250 ml, 100 mg:19.5 ml-100 mg:250 ml, 100 mg:20 ml-100 mg:250 ml, 100 mg:30 ml-100 mg:250 ml, 100 mg:35 ml-100 mg:250 ml, 100 mg:40 ml-100 mg:250 ml, 100 mg:45 ml-100 mg:250 ml, 100 mg:50 ml-100 mg:250 ml, 100 mg:55 ml-100 mg:250 ml, 100 mg:60 ml-100 mg:250 ml, 100 mg:65 ml-100 mg:250 ml, 100 mg:70 ml-100 mg:250 ml, 100 mg:75 ml-100 mg:250 ml, 100 mg:80 ml-100 mg:250 ml, 100 mg:85 ml-100 mg:250 ml, 100 mg:90 ml-100 mg:250 ml, 100 mg:95 ml-100 mg:250 ml, 100 mg:100 ml-100 mg:250 ml, 100 mg:105 ml-100 mg:250 ml, 100 mg:110 ml-100 mg:250 ml, 100 mg:120 ml-100 mg:250 ml, 100 mg:130 ml-100 mg:250 ml, 100 mg:140 ml-100 mg:250 ml, 100 mg:150 ml-100 mg:250 ml, 100 mg:160 ml-100 mg:250 ml, 100 mg:170 ml-100 mg:250 ml, 100 mg:180 ml-100 mg:250 ml, 100 mg:190 ml-100 mg:250 ml, 100 mg:200 ml-100 mg:250 ml, 100 mg:210 ml-100 mg:250 ml, 100 mg:220 ml-100 mg:250 ml, 100 mg:230 ml-100 mg:250 ml, 100 mg:240 ml-100 mg:250 ml, or 100 mg:250 ml), wherein said total solvent is the sum of said first solvent and second solvent.

In an embodiment, preferably, said solution is allowed to stand at room temperature and volatize naturally to dryness to obtain said crystalline form.

In an embodiment, preferably, said solution is allowed to stand at a temperature of 30-80° C. (the temperature may be, for example, 30° C., 35° C.-80° C., 40° C.-80° C., 45° C.-80° C., 50° C.-80° C., 55° C.-80° C., 60° C.-80° C., 65° C.-80° C., 70° C.-80° C., 75° C.-80° C., 80° C. (preferably 40° C.)) until it volatizes to dryness to obtain said crystalline form.

The crystalline form of the present invention herein can also be prepared by applying the crystallization conditions of the present invention to a volatile crystallization method, a slurry crystallization method, an anti-solvent crystallization method, a diffusion crystallization method, or a crystallization method with a polymer template. The operational approaches of said volatile crystallization method, slurry crystallization method, anti-solvent crystallization method, diffusion crystallization method, and crystallization method with a polymer template are conventional technical means in the art.

When the description is made with respect to the case where the crystalline form substantially exhibits an X-ray powder diffraction pattern as shown in FIG. 2, the term "substantially" means that the pattern shown in the figure must contain at least the main peaks, which, as compared to the most intense peak in the pattern, have a relative intensity of greater than 10%, especially greater than 20%. However, those skilled in the art will realize that the relative intensities in the X-ray powder diffraction pattern may be subject to strong intensity variations due to preferred orientation effects.

Yet another object of the present invention is to provide a pharmaceutical composition comprising the crystalline form of compound 3-((L-valyl)amino)-3,3-dideuterium-1-propanesulfonic acid as described above, and a pharmaceutically acceptable carrier.

The present invention further provides use of the crystalline form of compound 3-((L-valyl)amino)-3,3-dideuterium-1-propanesulfonic acid as described above or the pharmaceutical composition as described above in preparation of a medication for prevention or treatment of an amyloid-O related disease in a subject in need thereof.

Chinese patent application No. 201710168819.2 discloses that said compound 3-((L-valyl)amino)-3,3-dideuterium-1-propanesulfonic acid is used in prevention or treatment of an amyloid-O related disease or condition in a patient in need thereof.

In an embodiment, preferably, said amyloid-O related disease is Alzheimer's disease, mild cognitive impairment (MCI), Down's syndrome, Hereditary Cerebral Hemorrhage with Amyloidosis of the Dutch-Type, cerebral amyloid angiopathy, a degenerative dementia, a dementia of mixed vascular and degenerative origin, vascular dementia, dementia associated with Parkinson's disease, dementia associated with progressive supranuclear palsy, dementia associated with cortical basal degeneration, or dementia associated with diffuse Lewy body type of Alzheimer's disease.

In an embodiment, preferably, said amyloid-O related disease is Alzheimer's disease, mild cognitive impairment, cerebral amyloid angiopathy, or degenerative dementia.

In an embodiment, preferably, said amyloid-O related disease is Alzheimer's disease.

In an embodiment, preferably, said subject is an ApoE4 positive (also referred to herein as "ApoE4+" or simply "ApoE4") subject. Said subject has at least one ε4 allele of the apolipoprotein E (ApoE) gene. An ApoE4 positive subject may carry one or two copies of the ApoE4 allele. The 4 allele of apolipoprotein E gene is the strongest genetic risk factor for patients with late-onset Alzheimer's disease (AD). AD patients with at least one ε4 allele account for 50%-60% of AD cases vs. 25% prevalence in healthy individuals. ApoE4+ AD patients suffer from risks of decreased age of onset, increased severity and accelerated progression of AD. Subjects with two ε4 alleles account for 10%-14% of the total number of AD patients and exhibit an even more aggressive disease progression. ε4 allele leads to an increased brain Aβ amyloid deposition, increased CSF tau and p-tau, and faster cognitive decline. In addition, demented patients carrying one or two ε4 alleles of ApoE are more likely to have AD, resulting in a significantly reduced rate of disease misdiagnosis in clinical studies (2% in ApoE4 patients vs. 42% in non-ApoE4 patients).

As used herein, the term "subject" includes living organisms with an amyloid-β related disease, or who are susceptible to or at risk of an amyloid-β related disease, e.g., due to a genetic predisposition or mutation. Examples of subjects include humans, monkeys, cows, rabbits, sheep, goats, pigs, dogs, cats, rats, mice, and transgenic species thereof. The term "subject" generally includes animals susceptible to states characterized by an amyloid-O related disease, e.g., mammals, e.g., primates and humans. The animal can also be an animal model for a disorder, e.g., a transgenic mouse model, and the like.

In an embodiment, said crystalline form of compound 3-((L-valyl)amino)-3,3-dideuterium-1-propanesulfonic acid and the pharmaceutical composition comprising the crystalline form may be administered using any suitable route or means, such as without limitation via oral, parenteral, intravenous, intraperitoneal, intramuscular, sublingual, topical, or nasal administration, via inhalation, or via such other routes as are known in the art.

It should be understood that the dosage or amount of compound and/or composition used, alone or in combination with one or more active compounds to be administered, depends on the individual case and is, as is customary, to be adapted to the individual circumstances to achieve an optimum effect. Dosing and administration regimens are within the purview of those skilled in the art, and appropriate doses depend upon a number of factors within the knowledge of the ordinarily skilled physician, veterinarian, or researcher (e.g., see Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)).

It should be understood that compounds and/or compositions provided herein may be used alone or in combination with other therapies. Non-limiting examples of other amyloid-β related disease therapies include cognitive enhancers (e.g., acetylcholinesterase inhibitors, NMIDA receptor antagonists), other amyloid-O binding compounds, and so on. Thus, compounds and/or compositions described herein may be administered alone or in combination with one or more additional therapy that may be available over-the-counter or by prescription. The latter can be administered before, after or simultaneously with the administration of the compounds and/or compositions described herein. U.S. Patent Application Publication No. 2005/0031651 (incorporated herein by reference) provides a long but non-exhaustive list of "therapeutic drugs" that can be useful, in combination, according to the invention. Non-limiting examples of therapeutic drugs to be used with the compounds or pharmaceutical compositions provided herein are therapeutic drugs useful in the prevention or treatment of Alzheimer's Disease (AD) or its symptoms, including but not limited to donepezil (Aricept™), memantine (Namenda™), rivastigmine (Exelon™), Galanthamine (Reminyl™) and R-flurbiprofen (Flurizan™). The compounds and compositions according to the present invention could also be combined with vaccines and antibodies for the prevention or treatment of AD.

The crystalline form of 3-((L-valyl)amino)-3,3-dideuterium-1-propanesulfonic acid provided herein has such advantages as high purity, good stability, low hygroscopicity, and better flow properties; the preparation method of the crystalline form is simple, the solvent is cheap and easy to obtain, and the crystallization conditions are mild.

DETAILED DESCRIPTION

Figure 1:
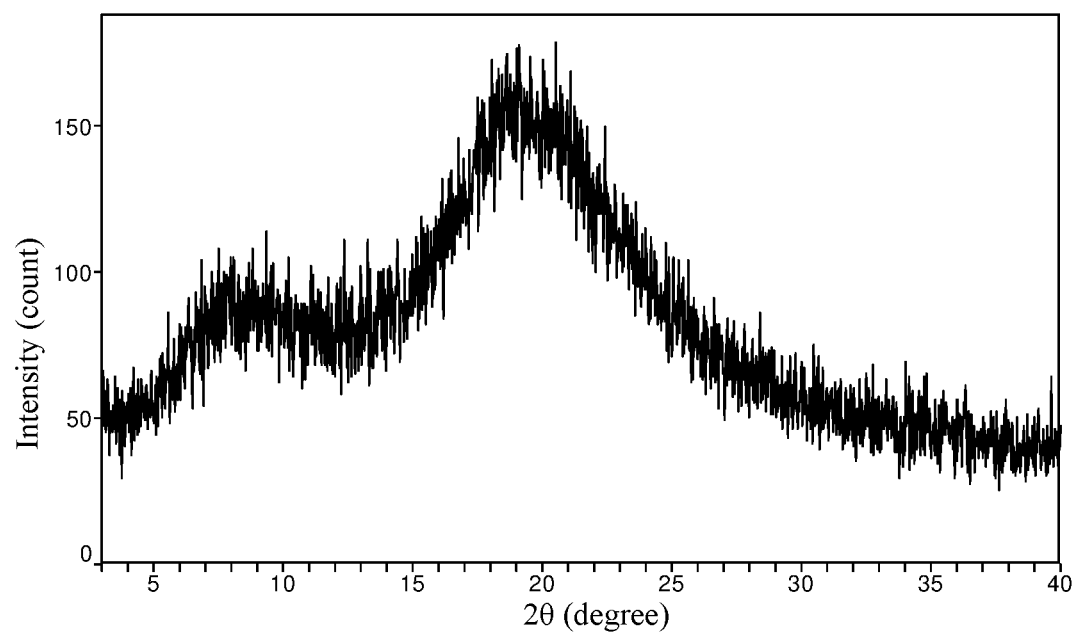
FIG. 1 is an X-ray powder diffraction (XRD) pattern of an amorphous compound 3-((L-valyl)amino)-3,3-dideuterium-1-propanesulfonic acid.

The present invention is further illustrated in detail by the following examples. Temperature is expressed in degrees Celsius. Unless stated otherwise, room temperature is in the range of 18-25° C. and the percentage is expressed by weight. The experimental methods under specific conditions are not specified in the following examples, and they are carried out according to conventional procedures and conditions, or according to the product instructions.

Abbreviations:
DMSO Dimethyl sulfoxide
DMF dimethylformamide
DSC differential scanning calorimetry
RH relative humidity
XRD X-ray powder diffraction
DCC N,N'-dicyclohexylcarbodiimide
eq equivalent The X-ray powder diffraction (XRPD) test instrument involved herein is Bruker D8 Advance diffractometer; detection conditions: Cu Kα radiation with X-ray of 1.54 Å, 40 kV/40 mA; detection angle: 3-40°2θ, scanning step: 0.02° 2θ; and scanning speed: 0.2 s·step$^{-1}$. Detection of environmental conditions: temperature=21° C., humidity=50%.

The X-ray single crystal diffraction analysis instrument involved herein is BrukerVenture; detection conditions: detection is carried out at a wavelength of 0.71073 Å at a temperature of 180 K.

The differential scanning calorimetry (DSC) instrument is the Q200 DSC instrument from TA Instruments; detection conditions: an aluminum crucible (with cover, but without perforation), a protective atmosphere of nitrogen, a gas flow rate of 40 mL/min, and the following common detection method: equilibrate at 20° C., and ramp rate of 10° C./min to 340° C. Detection of environmental conditions: temperature=20° C., humidity=56%.

The thermogravimetric analyzer (TGA) involved herein is Q500TGA from TA Instruments; detection conditions: a platinum crucible, a protective atmosphere of nitrogen, a gas flow rate of 40 mL/min; and the following detection method: a Hi-Res sensitivity of 3.0, ramp 10.00° C./min, res 5.0 to 150.00° C., and ramp 10.00° C./min to 350° C.

The dynamic vapor sorption (DVS) instrument involved herein is Q5000TGA from TA Instruments; detection conditions: a platinum crucible, a protective atmosphere of nitrogen, a gas flow rate of 10 mL/min; and the following detection method:

Equilibrate at at 25° C.;
Humidity of 0%;
Isothermal for 180 minutes;
Abort next iso if weight (%) <0.0100 for 15.00 min;
step humidity 10% every 120 min to 80.00%;
Abort next iso if weight (%) <0.0100 for 15.00 min;
step humidity 10% every 120 min to 0.00%.
Determination criteria:

| | |
|---|---|
| Non-hygroscopic | no more than 0.2% |
| Slightly hygroscopic | higher than 0.2%, but no more than 2.0% |
| hygroscopic | higher than 2%, but no more than 15% |
| Extremely hygroscopic | higher than 15% |

Example 1

Preparation of an Amorphous Compound 3-((L-valyl)amino)-3,3-dideuterium-1-propanesulfonic acid Step 1: Preparation of 3-amino-3,3-dideuterium-1-propanesulfonic acid sodium salt (1s)

A solution of 3-hydroxypropanenitrile (26.0 g, 366 mmol, 1.0 eq.) in anhydrous THF (50 mL) was slowly added dropwise to a solution of LiAlD$_4$ (10.0 g, 238 mmol, 0.65 eq.) in anhydrous THF (200 mL), and the reaction mixture was stirred overnight under reflux. After the reaction was cooled to room temperature, water (4.8 mL), a 15% NaOH aqueous solution (4.8 mL), and water (14.4 mL) were successively added for quenching, the mixture was stirred at room temperature for 2 hours, and then filtered to remove solid impurities. The filtrate was concentrated under reduced pressure and dried to give a red oily liquid which could be directly used in the next reaction step without purification.

The oily liquid (10.0 g, 128 mmol, 1.0 eq.) was dissolved in 100 mL of a chloroform solution and stirred in ice bath, and dichlorosulfoxide (18.2 g, 154 mmol, 1.2 eq.) was added thereto dropwise slowly. The reaction mixture was stirred overnight under reflux and the solvent was removed in a rotary evaporator, followed by concentration to give a black mixture. Purification by column chromatography gave 3-chloro-1,1-dideuterium-1-propylamine hydrochloride as a white solid (10.8 g, 64.4%).

The 3-chloro-1,1-dideuterium-1-propylamine hydrochloride (10.0 g, 76.3 mmol, 1.0 eq.) was dissolved in water (50 mL) and stirred, and $Na_2SO_3$ (9.61 g, 76.3 mmol, 1.0 eq.) was added thereto. The mixture was stirred overnight under reflux, and the solvent was distilled off in a rotary evaporator to give a white solid. The white solid was added into a concentrated hydrochloric acid, solid (sodium chloride) was removed through filtration, and the filtrate was concentrated under reduced pressure and dried to give a white solid, which was then recrystallized (with water-ethanol) and dried to give a white solid 3-amino-3,3-dideuterium-1-propanesulfonic acid (1) (9.5 g, 88.3%). $^1$H NMR (500 MHz, $D_2O$): δ ppm 2.15 (t, J=7.5 Hz, 2H), 3.07 (t, J=7.5 Hz, 2H); $^{13}$C NMR (125 MHz, $D_2O$): δ ppm 22.21, 37.74 (m, $CD_2$), 47.87; m/z (ES−) 140.0 (M−H).

The 3-amino-3,3-dideuterium-1-propanesulfonic acid was dissolved in 10 mL of water and equimolar amounts of sodium hydroxide was added thereto. The mixture was stirred at room temperature for 10 minutes, and then concentrated to dryness under reduced pressure to give a white solid 1s.

Step 2: preparation of 3-((L-valyl)amino)-3,3-dideuterium-1-propanesulfonic acid The 3-amino-3,3-dideuterium-1-propanesulfonic acid sodium salt is (1.63 g, 10.0 mmol, 1.0 eq) and N-tert-butoxycarbonyl-L-valine (2.60 g, 12.0 mmol, 1.2 eq.) were dissolved in anhydrous DMF (20 mL). After DCC (2.47 g, 12.0 mmol, 1.2 eq.) and HOBt (1.35 g, 10.0 mmol, 1.0 eq.) were added under ice bath conditions, the mixture was stirred overnight at room temperature. After water (2 mL) was added, the stirring was continued for 1 hour, the insoluble solids were removed through filtration, the filtrate was concentrated under reduced pressure to give a white solid crude. The solid was dissolved in water (20 mL) and extracted twice with ethyl acetate, the aqueous phase was concentrated under reduced pressure and then purified by column chromatography to give a while solid sodium 3-((N-tert-butoxycarbonyl-L-valyl)amino)-3,3-dideuterium-1-propanesulfonic acid (3.2 g, 88.3%). The while solid (3.2 g, 8.83 mmol, 1.0 eq.) was dissolved in a IN HCl solution (30 mL), stirred at 50° C. for 2 h, and concentrated under reduced pressure. The solid was dissolved in water (10 mL); after the Amberlite IR120 H-type ion exchange resins were added, stirring was conducted for 2 minutes; and the resins were removed through filtration. The ion exchange process was repeated, the filtrate was concentrated to dryness under reduced pressure to give an amorphous solid 3-((L-valyl)amino)-3,3-dideuterium-1-propanesulfonic acid (1.87 g, 88.1%). $^1$H NMR (500 MHz, $D_2O$): δ ppm 0.92-1.06 (m, 6H) 1.98 (t, J=7.5 Hz, 2H), 2.17-2.21 (m, 1H), 2.95 (t, J=8.0 Hz, 2H), 3.76 (d, J=6.5 Hz, 1H); $^{13}$C NMR (125 MHz, $D_2O$): δ ppm 17.01, 17.57, 23.73, 29.80, 48.40, 58.78, 169.18; m/z (ES−) 239.1 (M−H).

The X-ray powder diffraction (XRD) pattern of the amorphous solid is as shown in FIG. 1.

Example 2

Preparation of the Crystalline Form of 3-((1-valyl)amino)-3,3-dideuterium-1-propanesulfonic acid 3 g of the amorphous solid of 3-((L-valyl)amino)-3,3-dideuterium-1-propanesulfonic acid as prepared in Example 1 was dissolved in 10 mL water and heated to 60° C. to give a clear solution which was then stirred, and 100 mL of ethanol was added thereto. The mixture was cooled to room temperature and stirred for 1 hour; crystals were precipitated, filtered, and dried to give white crystals of 2.6 g with a purity of 100%, which white crystals were of Crystalline Form A.

Example 3

Characterization of Crystalline Form A of 3-((L-valyl)amino)-3,3-dideuterium-1-propane sulfonic acid According to the Present Example 2

1. X-Ray Powder Diffraction of Said Crystalline Form A

The determination was carried out using the aforementioned instruments, determination methods, operating conditions, and parameters. The result is shown in FIG. 2, and those specific data are shown in Table 1:

TABLE 1

Figure 2:
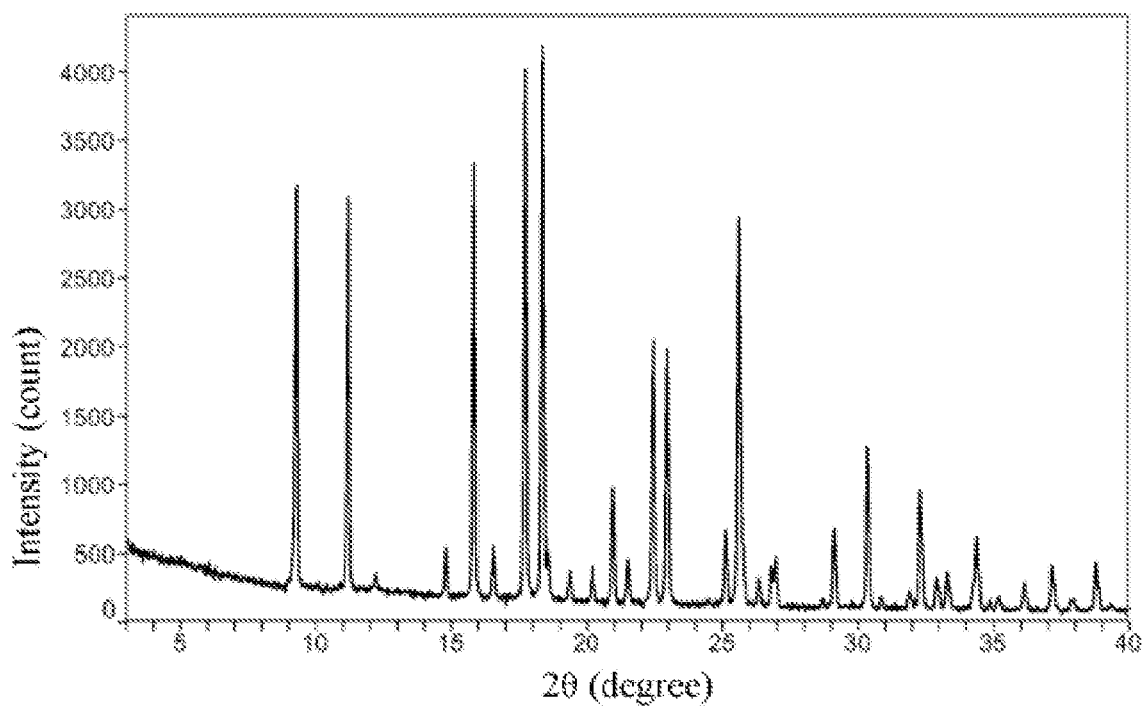
FIG. 2 is an X-ray powder diffraction (XRD) pattern of the crystalline form of 3-((L-valyl)amino)-3,3-dideuterium-1-propanesulfonic acid according to the present invention.

Data related to X-ray powder diffraction in FIG. 2

| Peak No. | 2θ diffraction angle (°) | Interplanar Spacing (Å) | Peak Height | Peak Height Relative Intensity (I %) | Peak Area | Peak Area Relative Intensity (I %) |
|---|---|---|---|---|---|---|
| 1 | 9.061 | 9.7514 | 1700 | 100.0 | 13990 | 100.0 |
| 2 | 10.991 | 8.0435 | 584 | 34.4 | 4944 | 35.3 |
| 3 | 11.981 | 7.3809 | 54 | 3.2 | 393 | 2.8 |
| 4 | 13.581 | 6.5145 | 34 | 2.0 | 141 | 1.0 |
| 5 | 14.585 | 6.0683 | 216 | 12.7 | 1654 | 11.8 |
| 6 | 15.629 | 5.6651 | 862 | 50.7 | 7426 | 53.1 |
| 7 | 16.320 | 5.4268 | 327 | 19.2 | 2577 | 18.4 |
| 8 | 17.505 | 5.0621 | 836 | 49.2 | 7558 | 54.0 |
| 9 | 18.156 | 4.8820 | 1203 | 70.8 | 11764 | 84.1 |
| 10 | 19.108 | 4.6408 | 343 | 20.2 | 2893 | 20.7 |
| 11 | 19.973 | 4.4419 | 136 | 8.0 | 1185 | 8.5 |
| 12 | 20.703 | 4.2867 | 1049 | 61.7 | 8827 | 63.1 |
| 13 | 21.294 | 4.1691 | 218 | 12.8 | 1768 | 12.6 |
| 14 | 22.183 | 4.0040 | 863 | 50.8 | 9017 | 64.5 |
| 15 | 22.734 | 3.9081 | 1020 | 60.0 | 9964 | 71.2 |
| 16 | 24.908 | 3.5718 | 137 | 8.1 | 1880 | 13.4 |
| 17 | 25.397 | 3.5042 | 854 | 50.2 | 9604 | 68.6 |
| 18 | 26.128 | 3.4078 | 159 | 9.4 | 1327 | 9.5 |
| 19 | 26.704 | 3.3355 | 152 | 8.9 | 1851 | 13.2 |
| 20 | 28.893 | 3.0876 | 272 | 16.0 | 2340 | 16.7 |
| 21 | 30.118 | 2.9647 | 418 | 24.6 | 4039 | 28.9 |
| 22 | 30.612 | 2.9181 | 57 | 3.4 | 335 | 2.4 |
| 23 | 31.677 | 2.8223 | 62 | 3.6 | 670 | 4.8 |
| 24 | 32.088 | 2.7870 | 338 | 19.9 | 3467 | 24.8 |
| 25 | 32.708 | 2.7357 | 80 | 4.7 | 539 | 3.9 |
| 26 | 33.079 | 2.7058 | 88 | 5.2 | 857 | 6.1 |
| 27 | 34.180 | 2.6211 | 209 | 12.3 | 2239 | 16.0 |
| 28 | 34.893 | 2.5692 | 78 | 4.6 | 936 | 6.7 |
| 29 | 35.865 | 2.5018 | 74 | 4.4 | 761 | 5.4 |
| 30 | 36.944 | 2.4311 | 115 | 6.8 | 1137 | 8.1 |

TABLE 1-continued

Data related to X-ray powder diffraction in FIG. 2

| Peak No. | 2θ diffraction angle (°) | Interplanar Spacing (Å) | Peak Height | Peak Height Relative Intensity (I %) | Peak Area | Peak Area Relative Intensity (I %) |
|---|---|---|---|---|---|---|
| 31 | 37.672 | 2.3858 | 100 | 5.9 | 919 | 6.6 |
| 32 | 38.602 | 2.3304 | 117 | 6.9 | 1271 | 9.1 |

2. X-Ray Single Crystal Diffraction Analysis of Said Crystalline Form A

Figure 3:
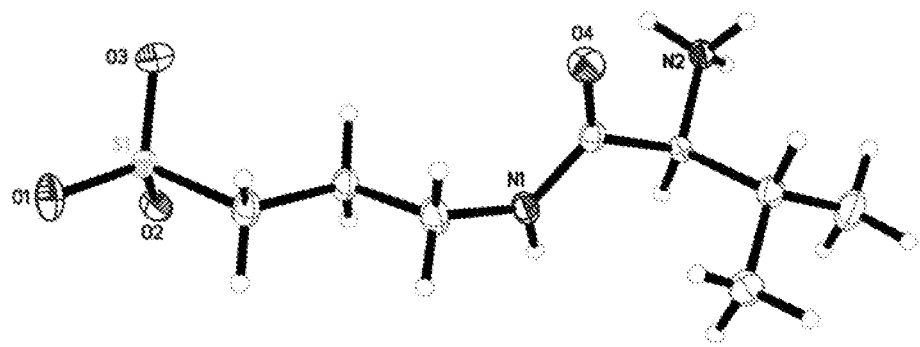
FIG. 3 is a diagram showing the structure and atomic number of the crystal of 3-((L-valyl)amino)-3,3-dideuterium-1-propanesulfonic acid according to the present invention.
Figure 4:
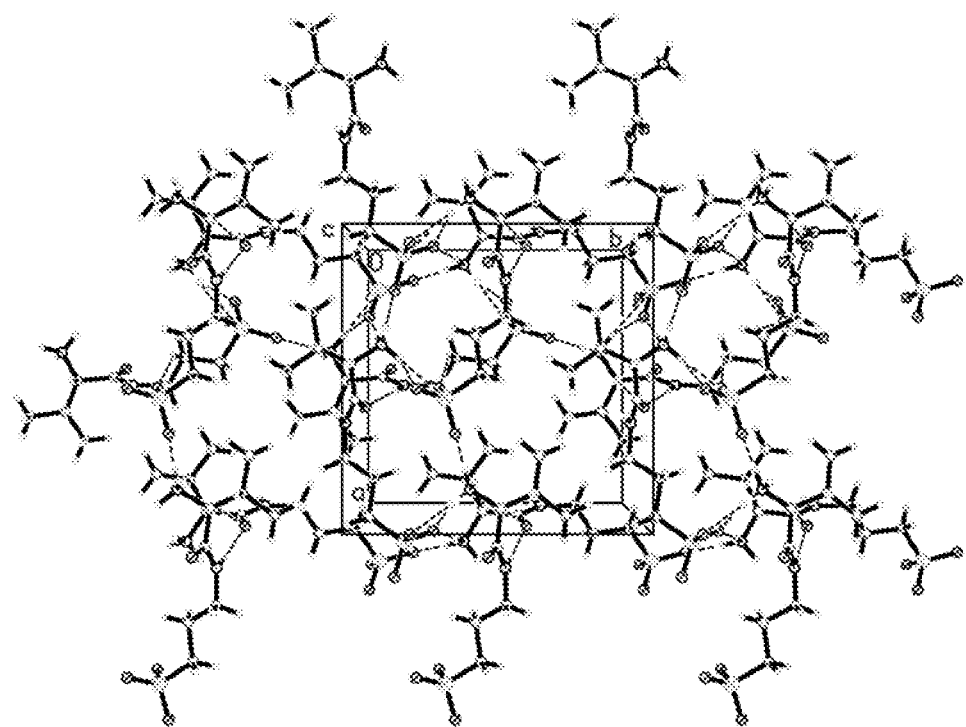
FIG. 4 is a unit cell packing diagram of the crystal of 3-((L-valyl)amino)-3,3-dideuterium-1-propanesulfonic acid according to the present invention.

The determination was carried out using the aforementioned instruments, determination methods, operating conditions, and parameters. The results are shown below and in Tables 2-3 and FIGS. 3-4.

The compound 3-((L-valyl)amino)-3,3-dideuterium-1-propanesulfonic acid according to the present invention has the molecular formula of $C_8H_{18}N_2O_4S$, a molecular weight of 238.30, a density of 1.383 $Mg/m^3$, F(000)=1024. Said Crystalline Form A is a white crystal, has a crystal size of 0.200×0.200×0.150 $mm^3$. Said Crystalline Form A belongs to a tetragonal system and has a space group of $P4_32_12$. The unit cell dimensions measured at a wavelength of 0.71073 Å at a temperature of 180K are as follows:

a=11.1989(4) Å, α=90, b=11.1989(4) Å, β=90°, c=18.2479(7) Å, γ=90°, Z=8, unit cell volume of 2288.57(19) Å3.

TABLE 2

Atomic coordinates (×10$^4$) and equivalent isotropic displacement parameters (Å$^2$ × 10$^3$) of Crystalline Form A of 3-((L-valyl)amino)-3,3-dideuterium-1-propanesulfonic acid

|  | x | Y | z | U(eq) |
|---|---|---|---|---|
| S(1) | 4285(1) | 6792(1) | 1087(1) | 16(1) |
| O(1) | 3039(1) | 6443(1) | 1155(1) | 27(1) |
| O(2) | 4642(1) | 7029(1) | 336(1) | 22(1) |
| O(3) | 4620(2) | 7782(2) | 1564(1) | 28(1) |
| O(4) | 8939(1) | 5298(1) | 2682(1) | 23(1) |
| N(1) | 8402(2) | 4698(2) | 1544(1) | 19(1) |
| N(2) | 11164(2) | 5926(2) | 2107(1) | 16(1) |
| C(1) | 5128(2) | 5545(2) | 1385(1) | 21(1) |
| C(2) | 6471(2) | 5727(2) | 1330(1) | 19(1) |
| C(3) | 7121(2) | 4672(2) | 1679(1) | 23(1) |
| C(4) | 9194(2) | 4989(2) | 2056(1) | 16(1) |
| C(5) | 10496(2) | 4865(2) | 1822(1) | 15(1) |
| C(6) | 11040(2) | 3698(2) | 2120(1) | 19(1) |
| C(7) | 10260(2) | 2623(2) | 1935(1) | 27(1) |
| C(8) | 12308(2) | 3521(2) | 1836(2) | 31(1) |

TABLE 3

Hydrogen coordinates (×10$^4$) and equivalent isotropic displacement parameters (Å$^2$ × 10$^3$) of Crystalline Form A of 3-((L-valyl)amino)-3,3-dideuterium-1-propanesulfonic acid

|  | x | Y | z | U(eq) |
|---|---|---|---|---|
| H(1A) | 8663 | 4513 | 1104 | 23 |
| H(2A) | 11789 | 6090 | 1804 | 25 |
| H(2B) | 11443 | 5766 | 2565 | 25 |
| H(2C) | 10666 | 6568 | 2125 | 25 |
| H(1B) | 4920 | 5370 | 1902 | 26 |
| H(1C) | 4903 | 4841 | 1088 | 26 |
| H(2D) | 6699 | 6475 | 1584 | 23 |
| H(2E) | 6706 | 5798 | 809 | 23 |
| H(3A) | 6977 | 4681 | 2215 | 28 |
| H(3B) | 6787 | 3920 | 1482 | 28 |

TABLE 3-continued

Hydrogen coordinates (×10$^4$) and equivalent isotropic displacement parameters (Å$^2$ × 10$^3$) of Crystalline Form A of 3-((L-valyl)amino)-3,3-dideuterium-1-propanesulfonic acid

|  | x | Y | z | U(eq) |
|---|---|---|---|---|
| H(5A) | 10540 | 4859 | 1275 | 18 |
| H(6A) | 11080 | 3765 | 2666 | 23 |
| H(7B) | 9481 | 2709 | 2174 | 40 |
| H(7C) | 10649 | 1892 | 2109 | 40 |
| H(7A) | 10149 | 2577 | 1403 | 40 |
| H(8C) | 12806 | 4198 | 1988 | 46 |
| H(8A) | 12296 | 3472 | 1300 | 46 |
| H(8B) | 12638 | 2781 | 2038 | 46 |

3. Differential Scanning Calorimetry (DSC) of said Crystalline Form A

Figure 5:
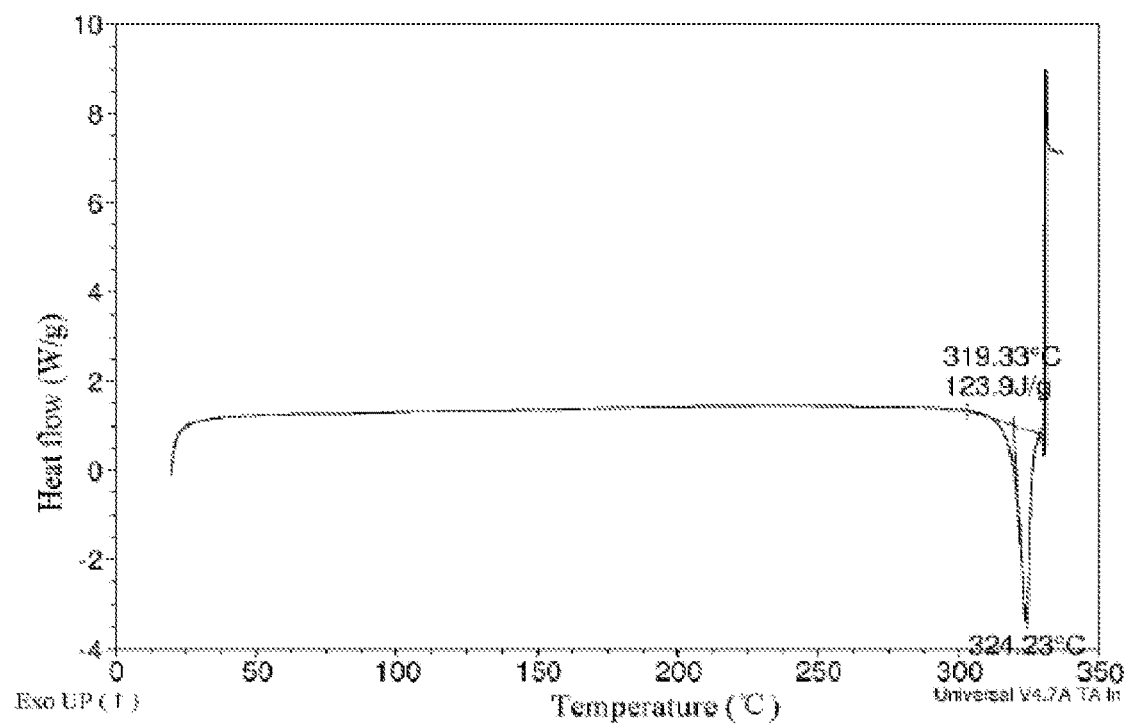
FIG. 5 illustrates differential scanning calorimetry (DSC) curves of the crystalline form of 3-((L-valyl)amino)-3,3-dideuterium-1-propanesulfonic acid according to the present invention. In the DSC curves, the characteristic endothermic peak occurs at a temperature between about 300° C. and 340° C. As shown in the DSC curves, said crystalline form has a melting point of 319° C.

The determination was carried out using the aforementioned instruments, determination methods, operating conditions, and parameters. The results are shown in FIG. 5. In the DSC curves, the characteristic endothermic peak occurs at a temperature between about 300° C. and 340° C. As shown in the DSC curves, said Crystalline Form A has a melting point of 319° C.

4. Thermogravimetric Analysis (TGA) of Said Crystalline Form A

Figure 6:
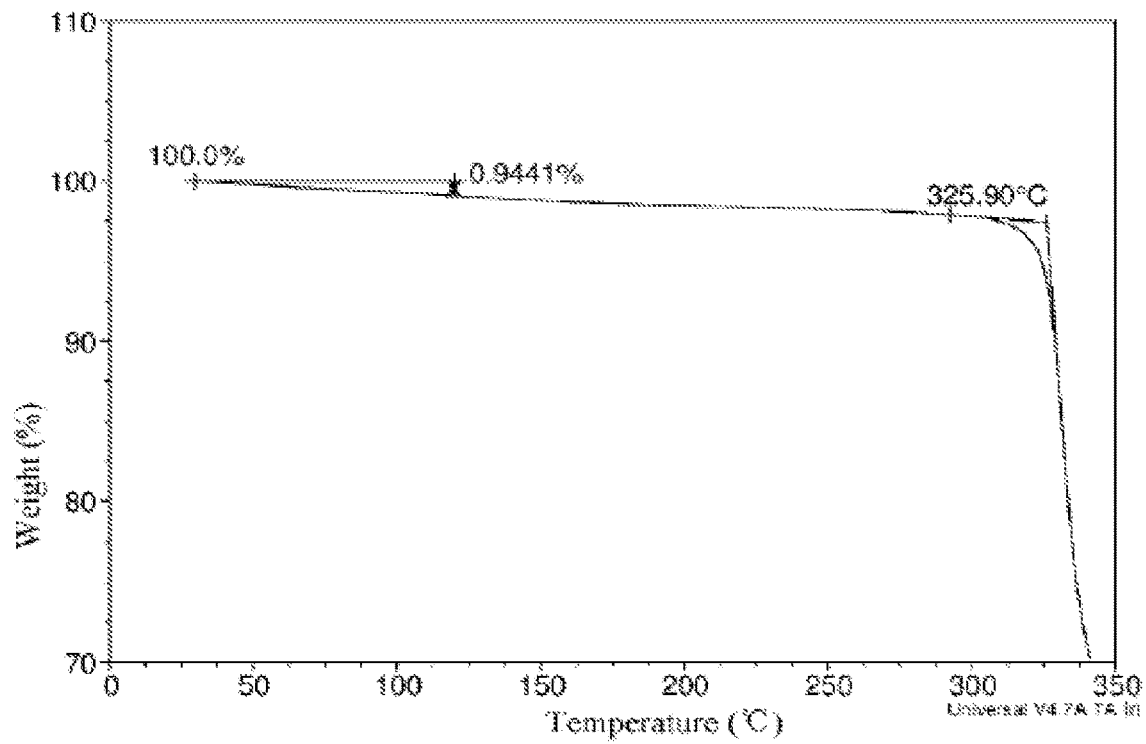
FIG. 6 is a thermogravimetric analysis diagram of the crystalline form of 3-((L-valyl)amino)-3,3-dideuterium-1-propanesulfonic acid according to the present invention, which shows that the crystalline form has a slow weight loss of about 0.9 wt % before 120° C., show that it is an anhydrate; and the decomposition temperature is about 326° C.

The determination was carried out using the aforementioned instruments, determination methods, operating conditions, and parameters. The results are shown in FIG. 6. The TGA diagram shows that the crystalline form has a slow weight loss of about 0.9 wt % before 120° C., indicating that it is an anhydrate; and the decomposition temperature is about 326° C.

5. Dynamic Vapor Sorption (DVS) Analysis of Said Crystalline Form A

Figure 7:
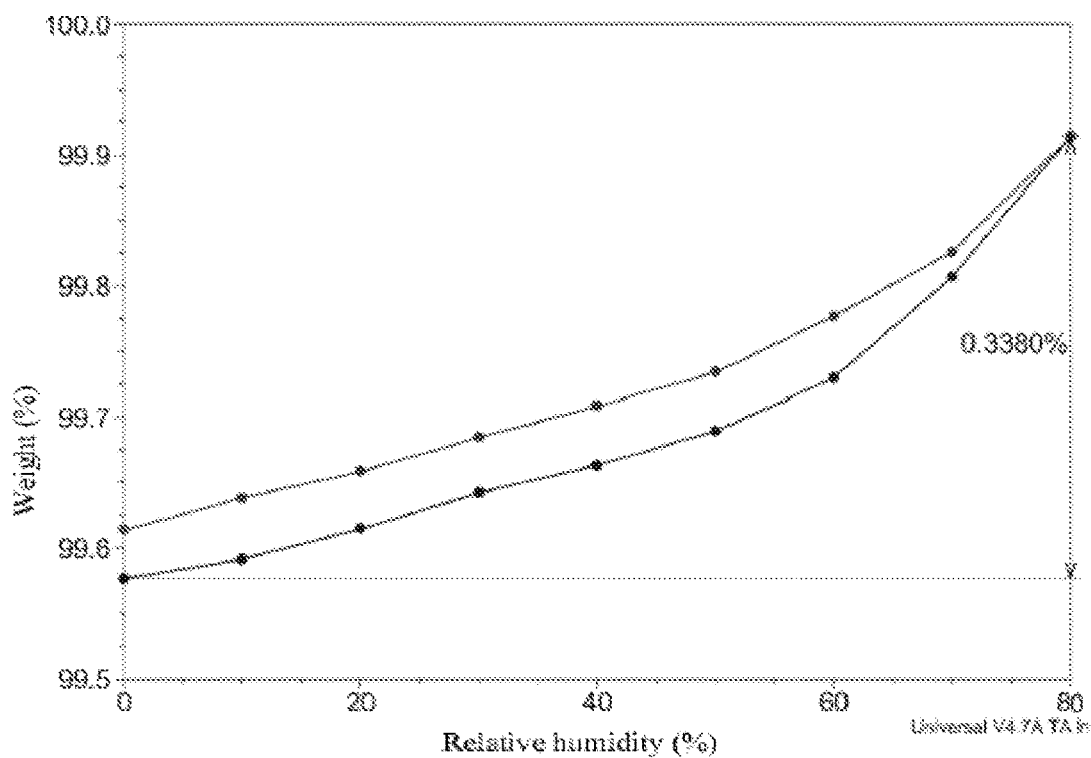
FIG. 7 is a Dynamic Vapor Sorption (DVS) isotherm diagram of the crystalline form of 3-((L-valyl)amino)-3,3-dideuterium-1-propanesulfonic acid according to the present invention, which shows that the crystalline form has a weight change of about 0.3 wt % in the range of from 0% RH to 80% RH, showing that it is slightly hygroscopic.

The determination was carried out using the aforementioned instruments, determination methods, operating conditions, and parameters. The results are shown in FIG. 7. The DVS isotherm diagram shows that the crystalline form has a weight change of about 0.3 wt % in the range of from 0% RH to 80% RH, showing that it is slightly hygroscopic.

Example 4

Preparation of a Crystalline Form of 3-((1-valyl)amino)-3,3-dideuterium-1-propanesulfonic acid About 100 mg of the solid of 3-((L-valyl)amino)-3,3-dideuterium-1-propanesulfonic acid as prepared in Example 1 was taken, and a crystalline form of 3-((L-valyl)amino)-3,3-dideuterium-1-propanesulfonic acid was prepared according to the method of Example 2, except that 0.5 mL of water and 20 mL of ethanol were used.

95 mg of white crystals were obtained with a purity of 100%, and was Crystalline Form A as characterized by XRD.

Example 5

Preparation of a Crystalline Form of 3-((L-valyl)amino)-3,3-dideuterium-1-propanesulfonic acid About 100 mg of the solid of 3-((L-valyl)amino)-3,3-dideuterium-1-propanesulfonic acid as prepared in Example 1 was taken, and a crystalline form of 3-((L-valyl)amino)-3,3-dideuterium-1-propanesulfonic acid was prepared according to the method of Example 2, except that 1 mL of water and 100 mL of ethanol were used.

95 mg of white crystals were obtained with a purity of 100%, and was Crystalline Form A as characterized by XRD.

Examples 6-40

Preparation of crystalline forms of 3-((L-valyl)amino)-3,3-dideuterium-1-propanesulfonic acid under different conditions by reference to the method of Example 2 was investigated, the resulting crystalline forms were characterized by XRD, and results were shown in Table 4 below.

TABLE 4

| Examples | First Solvent | Amount of the First Solvent (mL) | Second Solvent | Amount of the Second Solvent (mL) | Amount of Amorphous Solid of Example 1 (g) | Crystallization Temperature (° C.) | Crystalline Form |
|---|---|---|---|---|---|---|---|
| 6 | Water | 0.056 | Methanol | 3 | 0.01 | 60 | Crystalline Form A |
| 7 | Water | 0.056 | N-propanol | 3 | 0.01 | 60 | Crystalline Form A |
| 8 | Water | 0.056 | Isopropanol | 3 | 0.01 | 60 | Crystalline Form A |
| 9 | Water | 0.056 | Ethylene glycol | 3 | 0.01 | 60 | Crystalline Form A |
| 10 | Water | 0.056 | glycerin | 3 | 0.01 | 60 | Crystalline Form A |
| 11 | Water | 0.056 | Benzyl alcohol | 3 | 0.01 | 60 | Crystalline Form A |
| 12 | Water | 0.056 | Trifluoroethanol | 3 | 0.01 | 60 | Crystalline Form A |
| 13 | Water | 0.056 | Acetonitrile | 3 | 0.01 | 60 | Crystalline Form A |
| 14 | Water | 0.056 | Ethyl acetate | 3 | 0.05 | 40 | Crystalline Form A |
| 15 | Water | 0.056 | Isopropyl acetate | 3 | 0.05 | 40 | Crystalline Form A |
| 16 | Water | 0.1 | Acetone | 2 | 0.01 | 25 | Crystalline Form A |
| 17 | Water | 0.1 | Butanone | 2 | 0.01 | 25 | Crystalline Form A |
| 18 | Water | 0.1 | Methyl tert-butyl ether | 10 | 0.01 | 25 | Crystalline Form A |
| 19 | Water | 0.056 | Tetrahydrofuran | 3 | 0.01 | 60 | Crystalline Form A |
| 20 | Water | 0.056 | 1,4-dioxane | 3 | 0.01 | 60 | Crystalline Form A |
| 21 | Water | 0.05 | Trifluoroethanol | 1 | 0.015 | 40 | Crystalline Form A |
| 22 | Water | 0.1 | Toluene | 20 | 0.015 | 40 | Crystalline Form A |
| 23 | Water | 0.056 | Acetic acid | 4 | 0.01 | 60 | Crystalline Form A |
| 24 | Water | 0.1 | Dimethyl sulfoxide | 5 | 0.1 | 40 | Crystalline Form A |
| 25 | Water | 0.056 | N,N-dimethylformamide | 3 | 0.01 | 60 | Crystalline Form A |
| 26 | Water | 0.056 | N,N-dimethylacetamide | 4 | 0.01 | 60 | Crystalline Form A |
| 27 | Water | 1 | Trifluoroacetate | 20 | 0.01 | 60 | Crystalline Form A |
| 28 | Water | 0.5 | N-butanol | 20 | 0.1 | 60 | Crystalline Form A |
| 29 | Water | 0.5 | Tert-butanol | 20 | 0.1 | 60 | Crystalline Form A |
| 30 | DMSO | 1 | Methanol | 20 | 0.01 | 60 | Crystalline Form A |
| 31 | DMSO | 1 | Ethanol | 20 | 0.01 | 60 | Crystalline Form A |
| 32 | DMSO | 1 | Isopropanol | 20 | 0.01 | 60 | Crystalline Form A |
| 33 | DMSO | 1 | Acetone | 5 | 0.01 | 60 | Crystalline Form A |
| 34 | DMSO | 1 | Butanone | 5 | 0.01 | 60 | Crystalline Form A |

TABLE 4-continued

| Examples | First Solvent | Amount of the First Solvent (mL) | Second Solvent | Amount of the Second Solvent (mL) | Amount of Amorphous Solid of Example 1 (g) | Crystallization Temperature (° C.) | Crystalline Form |
|---|---|---|---|---|---|---|---|
| 35 | DMSO | 1 | Isopropyl acetate | 4 | 0.01 | 60 | Crystalline Form A |
| 36 | DMSO | 1 | Tetrahydrofuran | 5 | 0.01 | 60 | Crystalline Form A |
| 37 | DMSO | 1 | Acetonitrile | 4 | 0.01 | 60 | Crystalline Form A |
| 38 | DMSO | 1 | Toluene | 5 | 0.01 | 60 | Crystalline Form A |
| 39 | DMSO | 1 | N-butanol | 5 | 0.01 | 40 | Crystalline Form A |
| 40 | DMSO | 1 | Tert-butanol | 5 | 0.01 | 40 | Crystalline Form A |

Examples 41-46

About 10 mg of the amorphous solid of 3-((L-valyl)amino)-3,3-dideuterium-1-propanesulfnic acid as prepared in Example 1 was taken, and preparation of crystalline forms of 3-((L-valyl)amino)-3,3-dideuterium-1-propanesulfonic acid under different conditions was investigated using the slurry crystallization method at room temperature by reference to the principle of Example 2. Specifically, about 10 mg of said amorphous solid was taken and dissolved in said first solvent; the second solvent was added thereto to obtain a suspension, which was stirred at room temperature for 3 days; and the slurry suspension was centrifuged to obtain crystals. The results for characterization by XRD are shown in Table 5 below.

TABLE 5

| Examples | First Solvent | Amount of the First Solvent (mL) | Second Solvent | Amount of the Second Solvent (mL) | Crystalline Form |
|---|---|---|---|---|---|
| 41 | Water | 0.05 | Methanol | 1.0 | Crystalline Form A |
| 42 | Water | 0.1 | Ethanol | 2.0 | Crystalline Form A |
| 43 | Water | 0.1 | Isopropanol | 2.0 | Crystalline Form A |
| 44 | Water | 0.1 | Acetone | 2.0 | Crystalline Form A |
| 45 | Water | 0.05 | Tetrahydrofuran | 2.0 | Crystalline Form A |
| 46 | Water | 0.05 | Acetonitrile | 2.0 | Crystalline Form A |

Examples 47-50

About 10 mg of the amorphous solid of 3-((L-valyl)amino)-3,3-dideuterium-1-propanesulfnic acid as prepared in Example 1 was taken, and preparation of crystalline forms of 3-((L-valyl)amino)-3,3-dideuterium-1-propanesulfonic acid under different conditions was investigated using the slurry crystallization method at high temperature by reference to the principle of Example 2. Specifically, about 10 mg of said amorphous solid was taken and dissolved in said first solvent; the second solvent was added thereto to obtain a suspension, which was stirred at 40° C. for 3 days; and the slurry suspension was centrifuged to obtain crystals. The results for characterization by XRD are shown in Table 6 below.

TABLE 6

| Examples | First Solvent | Amount of the First Solvent (mL) | Second Solvent | Amount of the Second Solvent (mL) | Crystalline Form |
|---|---|---|---|---|---|
| 47 | Water | 0.05 | Trifluoroethanol | 1.0 | Crystalline Form A |
| 48 | Water | 0.1 | N-propanol | 2.0 | Crystalline Form A |
| 49 | Water | 0.1 | 1,4-dioxane | 2.0 | Crystalline Form A |
| 50 | Water | 0.1 | Acetonitrile | 2.0 | Crystalline FormA |

Examples 51-55

About 10 mg of the amorphous solid of 3-((L-valyl)amino)-3,3-dideuterium-1-propanesulfonic acid as prepared in Example 1 was taken, and preparation of crystalline forms of 3-((L-valyl)amino)-3,3-dideuterium-1-propanesulfonic acid under different conditions was investigated using the volatile crystallization method at room temperature. Specifically, about 10 mg of said amorphous solid was taken, said first solvent and second solvent were added thereto to obtain a clear solution, and the filtrate after filtration was placed at room temperature and naturally evaporated to dryness. The results for characterization by XRD are shown in Table 7 below.

TABLE 7

| Examples | First Solvent | Amount of the First Solvent (mL) | Second Solvent | Amount of the Second Solvent (mL) | Crystalline Form |
|---|---|---|---|---|---|
| 51 | Water | 0.05 | Methanol | 0.4 | Crystalline Form A |
| 52 | Water | 0.2 | Ethanol | 0.4 | Crystalline Form A |
| 53 | Water | 0.2 | Acetone | 0.2 | Crystalline Form A |
| 54 | Water | 0.2 | Tetrahydrofuran | 0.4 | Crystalline Form A |
| 55 | Water | 0.15 | Acetonitrile | 0.2 | Crystalline Form A |

Examples 56-60

About 10 mg of the amorphous solid of 3-((L-valyl)amino)-3,3-dideuterium-1-propanesulfonic acid as prepared in Example 1 was taken, and preparation of crystalline forms of 3-((L-valyl)amino)-3,3-dideuterium-1-propanesulfonic acid under different conditions was investigated using the volatile crystallization method at high temperature. Specifically, about 10 mg of said amorphous solid was taken, said first solvent and second solvent were added thereto to obtain a clear solution, and the filtrate after filtration was placed at room temperature and naturally evaporated to dryness. The results for characterization by XRD are shown in Table 8 below.

TABLE 8

| Examples | First Solvent | Amount of the First Solvent (mL) | Second Solvent | Amount of the Second Solvent (mL) | Crystalline Form |
|---|---|---|---|---|---|
| 56 | Water | 0.1 | Methanol | 0.4 | Crystalline Form A |
| 57 | Water | 0.1 | Trifluoroethanol | 0.4 | Crystalline Form A |
| 58 | Water | 0.1 | Isopropanol | 0.3 | Crystalline Form A |
| 59 | Water | 0.1 | 1,4-dioxane | 0.3 | Crystalline Form A |
| 60 | Water | 0.1 | Acetonitrile | 0.3 | Crystalline Form A |

Example 61

Stability Test of the Crystalline Form A According to the Present Invention

1. Detection Method

Sample and experimental preparation: the Crystalline Form A as prepared in Example 2 was taken as a sample; a proper amount of the sample was weighted and placed on a watch glass to form a thin layer of about 3~5 mm in thickness.

Experimental conditions: conventional (sealed and kept in darkness at 25° C.), long-term (uncovered and kept in darkness with ~60% RH at 25° C.), and accelerated (uncovered and kept in darkness with ~75% RH at 40° C.) conditions.

Figure 8:
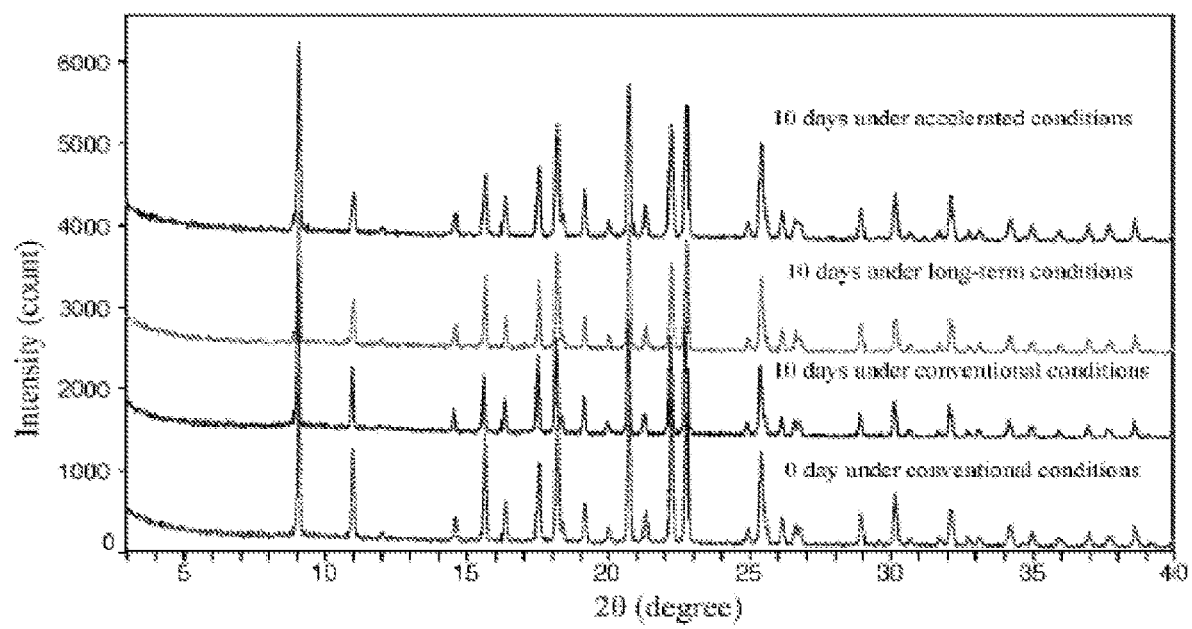
FIG. 8 is the XRD pattern showing the stability of the crystalline form of 3-((L-valyl)amino)-3,3-dideuterium-1-propanesulfonic acid according to the present invention.
Figure 9:
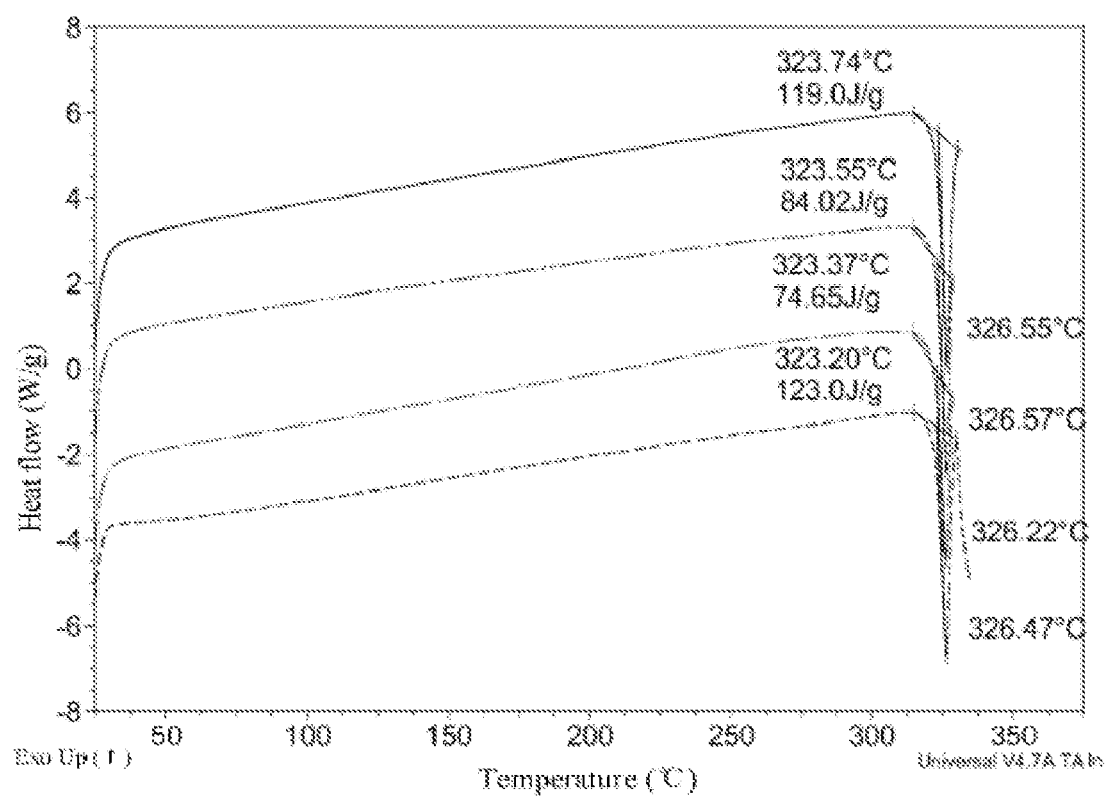
FIG. 9 illustrates the DSC curves showing the stability of the crystalline form of 3-((L-valyl)amino)-3,3-dideuterium-1-propanesulfonic acid according to the present invention.

Detection time: Day 0, Day 10.
Detected items: crystalline forms (XRD test), and melting points (DSC test).
Results:
Crystalline form: no change was detected in Crystalline Form A within 10 days under conventional, long-term and accelerated conditions. The specific results are shown in FIG. 8.
Melting point: there was no significant change in peak shape of the endothermic peak of said Crystalline Form A within 10 days under conventional, long-term and accelerated conditions, and the melting point varied at ±1° C. The specific results are shown in FIG. 9.

As can be seen from the above, said Crystalline Form A is the most stable crystalline form at room temperature, and no change has been detected in the crystalline form (by XRD detection) or in its melting point (by DSC detection) within 10 days under long-term and accelerated conditions. It can be seen from the above data that the crystalline form has excellent stability, better meets the quality requirements of pharmaceutical production, and is easy to store for long periods.

The present invention is not limited by the examples shown and described above, but may vary within the scope of the claims.

What is claimed is:

1. A crystalline form of compound 3-((L-valyl)amino)-3,3-dideuterium-1-propanesulfonic acid, characterized in that said crystalline form exhibits characteristic diffraction peaks at 2θ diffraction angles of 9.1°, 11.0°, 15.6°, 18.2°, 20.7°, and 22.2° in an X-ray powder diffraction pattern using Cu-Kα as a radiation source, wherein 2θ has an error range of ±0.2°.

2. The crystalline form as recited in claim 1, wherein said crystalline form exhibits characteristic diffraction peaks at 2θ diffraction angles of 9.1°, 11.0°, 14.6°, 15.6°, 16.3°, 17.5°, 18.2°, 19.1°, 20.7°, 22.2°, 22.7°, and 25.4° in the X-ray powder diffraction pattern, wherein 2θ has an error range of ±0.2°.

3. The crystalline form as recited in claim 1, wherein said crystalline form exhibits characteristic diffraction peaks at 2θ diffraction angles of 9.1°, 11.0°, 14.6°, 15.6°, 16.3°, 17.5°, 18.2°, 19.1°, 20.7°, 21.3°, 22.2°, 22.7°, 24.9°, 25.4°, 28.9°, 30.1°, 32.1°, and 34.2° in the X-ray powder diffraction pattern, wherein 2θ has an error range of ±0.2°.

4. The crystalline form as recited in claim 1, wherein said crystalline form has an X-ray powder diffraction pattern as shown in FIG. 2.

5. The crystalline form as recited in claim 1, wherein said crystalline form has a space group of $P4_32_12$, unit cell dimensions: a=11.1989(4) Å, α=90°, b=11.1989(4) Å, β=90°, c=18.2479(7) Å, γ=90°, Z=8, and has a unit cell volume of 2288.57(19) Å3.

6. The crystalline form as recited in claim 5, wherein said crystalline form belongs to a tetragonal system.

7. The crystalline form as recited in claim 6, wherein said crystalline form has a crystal size of 0.200×0.200×0.150 mm$^3$.

8. The crystalline form as recited in claim 1, wherein said crystalline form has a melting point of 319° C. as measured by differential scanning calorimetry.

9. A method for preparing the crystalline form of compound 3-((L-valyl)amino)-3,3-dideuterium-1-propanesulfonic acid as recited in claim 1, characterized in that said method comprises the following steps:
dissolving the compound 3((L-valyl)amino)-3,3-dideuterium-1-1propanesulfonic acid in a first solvent selected from the group consisting of water and dimethyl sulfoxide to obtain a clear solution; and adding a second solvent, stirring, precipitating crystals to obtain said crystalline form, wherein the first solvent is different from the second solvent.

10. The method as recited in claim 9, wherein before adding the second solvent, a solution of the 3-((L-valyl) amino)-3,3-dideuterium-1-propanesulfonic acid in the first solvent is heated to a temperature of 30-80° C.; and/or, after adding the second solvent, the solution is cooled to a temperature of 60° C. to −20° C. to precipitate crystals.

11. The method as recited in claim 10, wherein said second solvent is one or more selected from the group consisting of alcohols, nitriles, esters, ketones, ethers, alkanes, halogenated alkanes, aromatic hydrocarbons, organic acids, sulfoxides, amides, and nitromethane solvent.

12. The method as recited in claim 11, wherein said second solvent is one or more selected from the group consisting of methanol, ethanol, n-propanol, isopropanol, n-butanol, sec-butanol, ethylene glycol, glycerol, benzyl alcohol, trifluoroethanol, acetonitrile, propionitrile, butyronitrile, isobutyronitrile, ethyl formate, propyl formate, isopropyl formate, methyl acetate, ethyl acetate, isopropyl acetate, acetone, butanone, 2-pentanone, ethyl ether, isopropyl ether, methyl tert-butyl ether, tetrahydrofuran, 1,4-dioxane, n-hexane, n-heptane, methylcydohexane, dichloromethane, chloroform, toluene, acetic acid, dimethyl sulfoxide, N, N-dimethylformam ide, N, N-dimethylacetam ide, and nitromethane.

13. The method as recited in claim 10, wherein a volume ratio of said first solvent to said second solvent is 1:1-1:200; and/or, a mass-to-volume ratio of said compound 3-((L-valyl)amino)-3,3-dideuterium-1-propanesulfonic acid to the total solvent is 10 mg:0.05 ml-100 mg:250 ml, wherein said total solvent is the sum of said first solvent and second solvent.

14. The method as recited in claim 9, wherein after an addition of the second solvent, the solution is allowed to stand and volatize to precipitate crystals, thereby obtaining said crystalline form.

15. The method as recited in claim 14, wherein said first solvent is water, and said second solvent is one or more selected from the group consisting of alcohols, nitriles, esters, ketones, and ethers solvents.

16. The method as recited in claim 14, wherein said second solvent is one or more selected from the group consisting of methanol, ethanol, n-propanol, isopropanol, n-butanol, sec-butanol, trifluoroethanol, acetonitrile, propionitrile, butyronitrile, isobutyronitrile, ethyl formate, propyl formate, isopropyl formate, methyl acetate, ethyl acetate, isopropyl acetate, acetone, butanone, 2-pentanone, ethyl ether, isopropyl ether, methyl tert-butyl ether, tetrahydrofuran, and 1,4-dioxane.

17. The method as recited in claim 14, wherein a volume ratio of said first solvent to said second solvent is 1:1-1:100; and/or, a mass-to-volume ratio of said compound 3-((L-valyl)amino)-3,3-dideuterium-1-propanesulfonic acid to the total solvent is 10 mg:0.05 ml-100 mg:250 ml, wherein said total solvent is the sum of said first solvent and second solvent.

18. The method as recited in claim 14, wherein said solution is allowed to stand at room temperature and volatize naturally to dryness to obtain said crystalline form.

19. The method as recited in claim 14, wherein said solution is allowed to stand at a temperature of 30-80° C. until it volatizes to dryness to obtain said crystalline form.

20. A pharmaceutical composition comprising the crystalline form of compound 3-((L-valyl)amino)-3,3-dideuterium-1-propanesulfonic acid as recited in claim 1, and a pharmaceutically acceptable carrier.

21. A method of treatment of an amyloid-β related disease in a subject in need thereof comprising administering to the subject a therapeutically effective amount of a crystalline form as recited in claim 1.

22. The method as recited in claim 21, wherein said amyloid-β related disease is Alzheimer's disease, mild cognitive impairment (MCI), Down's syndrome, Hereditary Cerebral Hemorrhage with Amyloidosis of the Dutch-Type, cerebral amyloid angiopathy, a degenerative dementia, a dementia of mixed vascular and degenerative origin, vascular dementia, dementia associated with Parkinson's disease, dementia associated with progressive supranuclear palsy, dementia associated with cortical basal degeneration, or dementia associated with diffuse Lewy body type of Alzheimer's disease.

23. The method as recited in claim 21, wherein said subject is an ApoE4 positive subject.

24. A method of treatment of an amyloid-β related disease in a subject in need thereof comprising administering to the subject a therapeutically effective amount of a pharmaceutical composition as recited in claim 20.

* * * * *